United States Patent [19]

Kidron et al.

[11] Patent Number: 4,579,730

[45] Date of Patent: Apr. 1, 1986

[54] PHARMACEUTICAL COMPOSITIONS CONTAINING INSULIN

[75] Inventors: Miriam Kidron, Jerusalem; Ehud Ziv, Motza Ilit; Hanoch Bar-On; Amiram Eldor, both of Jerusalem, all of Israel

[73] Assignee: Hadassah Medical Organization, Israel

[21] Appl. No.: 608,462

[22] Filed: May 9, 1984

[30] Foreign Application Priority Data

May 23, 1983 [IL] Israel ................................. 68769

[51] Int. Cl.$^4$ ......................... A61K 9/50; A61K 9/28; A61K 37/26
[52] U.S. Cl. ....................................... 424/19; 424/32; 424/35; 514/3
[58] Field of Search ................... 424/19, 32, 35, 178

[56] References Cited

FOREIGN PATENT DOCUMENTS

| | | |
|---|---|---|
| 127535 | 12/1984 | European Pat. Off. . |
| 2640707 | 3/1978 | Fed. Rep. of Germany . |
| 2515960 | 5/1983 | France . |
| 49-175631 | 5/1974 | Japan . |
| 52-57313 | 5/1977 | Japan . |

OTHER PUBLICATIONS

Sarrach Stud. Biophys 100(2):95–102 (1984).
Leung et al., Artif. Organs 7(2): 208–212 (1983).
Chang, J. Bioeng. 1(1):25–32 (1976).
Ziv et al., Life Sci. 29(8):803–809 (1981).

*Primary Examiner*—Shep K. Rose
*Attorney, Agent, or Firm*—Darby & Darby

[57] ABSTRACT

The invention provides a pharmaceutical composition for the oral administration of insulin comprising insulin, a bile acid or alkali metal salt thereof, the bile acid being selected from the group consisting of cholic acid, chenodeoxycholic acid, taurocholic acid, taurochenodeoxycholic acid, glycocholic acid, glycochenocholic acid, 3$\beta$-hydroxy-12-ketocholic acid, 12$\alpha$-3$\beta$-dihydrocholic acid, and ursodesoxycholic acid, and a protease inhibitor, the composition being provided with an enterocoating to assure passage through the stomach and release in the intestine.

4 Claims, No Drawings

PHARMACEUTICAL COMPOSITIONS CONTAINING INSULIN

The present invention relates to a pharmaceutical composition containing insulin. More particularly, the present invention relates to a pharmaceutical composition for the oral administration of insulin.

Insulin is a medicament particularly useful as a hypoglycaemic agent being widely used by patients suffering from diabetes and is the only treatment for Juvenile diabetes mellitus.

In practice today insulin is administered only by injection. The everyday injection of insulin is very troublesome and causes considerable physical and even mental suffering for the patients. Several severe side effects such as lipodystrophy at the site of the injection, lipoatrophy, lipohypertrophy or occasional hypoglycemia have been noted and reported to occur.

To avoid the daily injection of the drug, the insulin pump has been developed in the last decade. This pump, however, also suffers from some of the disadvantages of the daily injection. Since insulin is normally secreted into the portal vein, normally the liver is exposed to a greater insulin concentration than peripheral tissues. Insulin administered via the peripheral venous system to insulin-deficient diabetic patients results in a concentration of insulin in the portal vein almost equal to that in the peripheral circulation. The net result is hypoinsulinemia in the portal vein and the liver and hyperinsulinemia in the peripheral venous system. This may lead to an abnormal pattern of glucose disposal.

In order to overcome the difficulties caused by injection of insulin, rectal administration of insulin has recently been proposed, studied and developed.

Shichiri et al. (J. Pharm. Pharmac. 30, 806–808, 1978), Bar-On et al. (Br. J. Pharmac. 73, 21–24, 1981), and others tested the hypoglyceaemic affect of insulin mixed with polyoxyethylen lauryl ether or polyoxtethylene-20-cetyl ether by administering through the rectum. Ziv et al (Life Sciences, 29, 803–809, 1981) tested the same effect with insulin mixed with bile salts. The insulin effected the blood glucose levels, by reduction of approximately 50%, with dose of 48 $\mu$/kg.

In a further article by Ziv, Kidron, Bar-On and Berry (Life Sciences, 31, pp. 2837–2841, 1982) insulin was used as a model for proteins in general to discover the theoretical question of protein absorption through the intestine and it was found that in the presence of the strong detergent effect of deoxycholic acid and soybean trypsin inhibitor, biologically active macromolecules such as insulin could be effectively absorbed from the intestine.

Similarly, in British Pat. No. 1,563,311 there is described and claimed a pharmaceutical composition for rectal administration which comprises insulin, a carrier suiting the composition for rectal administration, and an agent for increasing the rate of absorption of the insulin into the body on rectal administration of the composition, the agent comprising at least one material selected from (a) nonionic polyoxyethylene ether surface active agents having an HLB value of 6 to 19 and wherein the average number of polyoxyethylene units is 4 to 30, (b) anionic surface active agents, (c) cationic surface active agents, (d) ampholytic surface active agents, (e) bile acids and (f) alkali metal salts of bile acids and amounting to 0.001 to 0.5 times the weight of the carrier. In U.S. Pat. Nos. 4,434,159 and 4,164,573 there are described similar insulin containing pharmaceutical compositions for rectal administration.

Thus the administration of insulin through the portal system of the human rectum in suppository form or further along the intestinal tract, e.g., by enema-like introduction is suggested and taught by said articles and patent.

Nevertheless it has been found that only part of the insulin is absorbed through the portal system from the human rectum and rectal administration also represents a major inconvenience for the patient.

According to the present invention, there have now been developed pharmaceutical compositions for administering insulin which overcome all of the above-mentioned disadvantages of the prior art systems.

More specifically, there have now been discovered and provided according to the present invention pharmaceutical compositions for the oral administration of insulin comprising insulin, a bile acid or alkali metal salt thereof, said bile acid being selected from the group consisting of cholic acid, chenodeoxycholic acid, taurocholic acid, taurochenodeoxycholic acid, glycocholic acid, glycochenocholic acid, 3$\beta$-monohydroxychloric acid, lithocholic acid, 3$\alpha$-hydroxy-12-ketocholic acid, 3$\beta$-hydroxy-12-ketocholic acid, 12$\alpha$-3$\beta$-dihydrocholic acid, and ursodesoxycholic acid, and a protease inhibitor, said composition being provided with an enterocoating to assure passage through the stomach and release in the intestine.

Thus there have now been discovered pharmaceutical compositions containing insulin which can be administered orally and which have the same effect as naturally secreted insulin on the blood glucose levels. The insulin administered according to the present invention reaches the intestine and is quickly absorbed in the body through the intestine and through the portal system to the liver. This absorption route is the most convenient way to administer the drug and it resembles the physiological secretion of insulin by the pancreas, thus enabling delicate control of the blood glucose level and the metabolic activities of the liver and the peripheral organs controlled by insulin.

Various attempts have been made in the past to administer insulin orally. In one study it was shown that administration of liposome-entrapped insulin caused a significant reduction of blood glucose levels in diabetic rats (Dapergolas, G. and Gregoriadis, Lancet ii, 824–827, 1976). Patel and Ryman (FEBS Letters, 62, 60–63, 1976) showed that insulin administered orally entrapped in liposomes is effective in diabetic rats. PapahadJopoulos and SJoka (U.S. Pat. No. 4,235,871) suggested to use liposomes to encapsulate insulin and Sears (U.S. Pat. No. 4,145,410) used synthetic phosphatidyl compounds to stabilize the liposomes against lipolysis.

Another approach for insulin enhanced activity is the addition of an adjuvant such as choline (which is not a bile salt) to the insulin injections (U.S. Pat. No. 2,563,070). This is totally different from oral administration with bile salts since the bile salts in an oral composition enhance the absorption of insulin from the intestinal luman to the blood circulation while with injectable solutions no such absorption takes place or is necessary and the function of chlorine which is different structurally and chemically from cholic acid is entirely different in said patent and is intended to delay the insulin absorption.

Thus it will be realized that none of the said publications teaches or suggests the novel pharmaceutical composition of the present invention which includes the use of bile salts to promote the absorption of insulin, the use of protease inhibitors to protect insulin against proteolysis and the use of enterocoating of the active mixture.

Human insulin including human insulin genetically reproduced or any insulin such as, for example, the insulin obtained from cows (bovine), pigs or whales can be used as the insulin for compositions of this invention. Furthermore, metal complexes of insulin such as the zinc complex of insulin as well as protamine zinc insulin and globin zinc insulin may be also used as the insulin in compositions of this invention.

The protease inhibitor used in the compositions of the present invention can be any material which has the ability to inhibit any proteolytic activity.

Practical examples of such protease inhibitors include aprotinin (Trasilol ® of Bayer), Pentamidine isethionate, antipain, tosylamide-phenylethyl-chloromethyl ketone (TPCK), phenylmethyl sulfonyfluoride (PMSF), pepstatin, trypsin inhibitor, Acetone, Alcohols, guanidium, $a_2$-macroglubulin, TLCK, Chelating agents of Zn, Iodoacetate, $a_1$-antitrypsin, EDTA, Zn, Antithrombin III, leupeptin, Trypsin inhibitor from soy bean, trypsin inhibitor from hen egg white, trypsin inhibitor from chicken egg white, etc.

Some of the above protease inhibitors might be toxic in large doses and therefore, if chosen the use and dosage thereof must be carefully screened and tested.

In expecially preferred embodiments of the present invention said protease inhibitor is selected from the group consisting of aprotinin, $A_2$-macroglobulin, antithrombin III and trypsin inhibitor from soy bean or chicken egg white.

The most preferred protease inhibitor agents used in this invention are preferably Trasylol ® in the amount of 1000 k.i.u./100 mg pill, or 3 mg soybean trypsin inhibitor or 10 mg soybean flour.

The above-mentioned bile acids and alkali metal salts thereof used in the oral compositions of the present invention promote the absorption of the insulin from the intestinal tract and act as carriers therefor, however, it was interesting and surprising to note that deoxycholic acid, which was the acid of choice in the article in Life Sciences, Vol. 31, pp. 2837-2441 (1982) is unsuitable for use in the oral compositions of the present invention because of the damage which it causes to the cells of the intestinal wall.

The active concentration of bile acid or salt thereof is about 1-20 mg/ml and preferably about 5-15 mg/pill/one treatment.

It has also been surprisingly found that sodium cholate can simultaneously function both as the bile acid carrier of the insulin and the protease inhibitor agent and thus a composition comprising insulin and sodium cholate in an enteric coating is especially preferred.

The amount of insulin in a composition is 20-50 u/kg in rats and expected to be about 0.5-3 u/kg in humans. Preferred dosages for humans are about 1-2 u/kg/treatment with three treatments a day, however sustained release microencapsulation could allow treatment to be reduced to once or twice a day.

The enterocoating and possible microencapsulation of the mixture provides protection for the insulin against decomposition in the stomach and for the slow release of the mixture constituents in the intestinal tract.

The enterocoating is carried out by methods known per se in the art, e.g., according to Remington Pharmaceutical Sciences, p. 1614-1615 (1975, 15th Ed. Mack Pub. Co.) and Theory and Practice of Industrial Pharmacy, Lackman, Liberman & Canig, p. 116-117, 371-374 (1976, 2nd Ed.) as is the enteric microencapsulation (Theory and Practice of Industrial Pharmacy ibid, pp. 420-438).

One of the findings of the present invention is that there is different rate of absorption of the different constituents of the present composition from the intestinal lumen into the blood stream. The absorption of the bile acid is very fast, e.g., more than 50% of cholic acid is absorbed during 30 minutes while only 5-10% of the insulin is absorbed during 60 minutes.

For this reason a drug regimen involving ingestion of a pair of pills at spaced intervals, e.g., a second pill containing a higher concentration of bile acid to be taken half an hour after the first pill is contemplated as is microencapsulation of different constituents with spaced time release coatings to enhance the absorption of the insulin into the system.

While the invention will now be described in connection with certain preferred embodiments in the following examples it will be understood that it is not intended to limit the invention to these particular embodiments. On the contrary it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

An enterocoated capsule was prepared for oral administration of insulin to a diabetic dog. Table 1 shows Plasma 1R1 levels and glucose levels with administration.

TABLE I

| | Composition of this invention | | |
|---|---|---|---|
| Test No. | Formulation | Time (Min) | Glucose mm | Insulin $\mu$m/ml |
| | Oral administration | | | |
| 1. | insulin 7.3 u/kg | 0 | 36.7 | 15 |
| | cholate 30 mg | 15 | 33.9 | 0 |
| | soybean- | 30 | 34.4 | 6 |
| | trpsin inhibitor | 45 | 34.6 | 6 |
| | 20 mg | 60 | 33.8 | 12 |
| | in two capsules | 75 | 29.1 | 23 |
| | (enterocoated) | | | |
| | | 105 | 23.7 | 36 |
| | | 135 | 21.8 | 22 |
| | | 65 | 16.1 | 3 |
| | | 210 | 15.8 | 0 |
| | | 240 | 11.5 | 0 |
| | | 270 | 12.1 | 0 |
| | | 300 | 10.2 | 0 |
| | | 330 | 7.5 | 0 |
| | | 360 | 9.3 | 0 |

TABLE II

| | COMPARISON | | | |
|---|---|---|---|---|
| Test No. | Formulation | Time (Min.) | Glucose mm | Insulin μm/ml |
| | Insulin 0.5 u/kg intramuscular injection | 0 | 28.7 | 0 |
| | | 10' | 23.3 | 73 |
| | | 20' | 21.5 | 76 |
| | | 30' | 19.9 | 213 |
| | | 45' | 15.6 | 220 |
| | | 60' | 12.9 | 81 |
| | | 75' | 10.9 | 120 |
| | | 90' | 8.5 | 61 |
| | | 120' | 6.5 | 50 |
| | | 150' | 6.4 | 18 |
| | | 180' | 6.5 | 25 |

COMPARISON EXAMPLE A

A solution was prepared for direct intestinal administration of 0.5 ml in final volume. In the rat.

TABLE III

Compositions of this invention

| Test No. | Formulation | Percent decrease in blood glucose 60 min | 120 min | 240 min | No. of Animals tested |
|---|---|---|---|---|---|
| | Injection of 0.5 ml into the ileum | | | | |
| 1. | Insulin 24 u/kg sodium cholate 1% Trasylol 3000 K.I.U. in saline | −33 | −11 | +11 | 5 |
| 2. | Insulin 24 u/kg sodium cholate 1% in saline | −23 | −19 | +10 | 4 |
| 3. | Insulin 24 u/kg sodium cholate 0.5% Trasylol 3000 K.I.U. in saline | −18 | −24 | −2 | 6 |
| 4. | Insulin 48 u/kg sodium cholate 1% in saline | −34 | −20 | +10 | 10 |
| 5. | Insulin 48 u/kg sodium cholate 1% Trasylol 1000 u in salin | −55 | −50 | +3 | 6 |
| 6. | Insulin 48 u/kg sodium cholate 1% Trasylol 3000 u in saline | −61 | −66 | −25 | 6 |
| 7. | Insulin 48 u/kg sodium cholate 1% Soybean trypsin-inhibitor 3 mg in saline | −35 | −28 | +14 | 6 |
| 8. | Insulin 48 u/kg sodium taurocholate 1% in saline | −7 | −2 | +27 | 8 |
| 9. | Insulin 48 u/kg sodium taurocholate 1% Trasylol 1000 K.I.U. in saline | −28 | −20 | +21 | 6 |
| 10. | Insulin 48 u/kg sodium taurocholate 1% Trasylol 3000 K.I.U. in saline | −39 | −36 | +3 | 7 |
| 11. | Insulin 48 u/kg Sodium taurocholate 1% Soybean trypsin-inhibitor 3 mg in saline | −15 | −12 | +21 | 6 |
| 12. | Insulin 48 u/kg Trasylol 3000 K.I.U. in saline | −33 | −30 | +4 | 6 |
| | Control-intestinal administration | | | | |
| 13. | Insulin 48 u/kg in saline | −5 | −6 | +25 | 6 |

As is clear from the tables the effect of intestinal administration of insulin on blood glucose levels is similar to the effect of insulin injected to the animals. The effect is similar when insulin is given orally to the dog or directly into the intestine of the rat.

Enterocoating provides the sufficient shelter against the destruction of the insulin in the stomach and delays its effect for one hour in the dog.

Now the following examples illustrate practically the pharmaceutical compositions of insulin for oral use embodying this invention, wherein the dosage of insulin employed are for the human bodies.

All examples are for one pill or one capsule containing total weight of 100 mg. The active compounds will be given in detail. The complimentary weight is of inert compounds like manitol or avicel 101.

Thus the active ingredients and the vehicle for oral administration of compositions according to the present invention are hereinafter set forth in tabular form:

| Example | Amount Insulin | Bile Acid/Salt | Protease Inhibitor | Vehicle |
|---|---|---|---|---|
| 2. | 100 I.U. | 15 mg. sodium cholate | — | enterocoated capsule |
| 3. | 100 I.U. | 15 mg. sodium cholate | aprotinin 1000 K.I.U. | enterocoated capsule |
| 4. | 100 I.U. | 15 mg. sodium cholate | aprotinin 3000 K.I.U. | enterocoated capsule |
| 5. | 100 I.U. | 15 mg. sodium cholate | 5 mg. soybean trypsin inhibitor | enterocoated capsule |
| 6. | 100 I.U. | 15 mg. sodium cholate | — | enterocoated pills |
| 7. | 100 I.U. | 15 mg. sodium cholate | aprotinin 1000 K.I.U. | enterocoated pills |
| 8. | 100 I.U. | 15 mg. sodium cholate | aprotinin 3000 K.I.U. | enterocoated pills |
| 9. | 100 I.U. | 15 mg. sodium cholate | 5 mg. chicken egg white trypsin inhibitor | enterocoated pills |
| 10. | 100 I.U. | 15 mg. sodium taurocholate | aprotin 1000 K.I.U. | enterocoated capsule |
| 11. | 100 I.U. | 15 mg. sodium taurocholate | aprotinin 3000 K.I.U. | enterocoated capsule |

-continued

| Example | Amount Insulin | Bile Acid/Salt | Protease Inhibitor | Vehicle |
|---|---|---|---|---|
| 12. | 100 I.U. | 15 mg. sodium taurocholate | 5 mg. soybean trypsin inhibitor | enterocoated capsule |
| 13. | 100 I.U. | 15 mg. sodium taurocholate | aprotinin 1000 K.I.U. | enterocoated pills |
| 14. | 100 I.U. | 15 mg. sodium chenodeoxycholate | aprotinin 1000 K.I.U. | enterocoated capsule |
| 15. | 100 I.U. | 15 mg. sodium chenodeoxycholate | aprotinin 3000 K.I.U. | enterocoated capsule |
| 16. | 100 I.U. | 15 mg. sodium chenodeoxycholate | 5 mg. soybean trypsin inhibitor | enterocoated capsule |
| 17. | 100 I.U. | 15 mg. sodium chenodeoxycholate | aprotinin 1000 K.I.U. | enterocoated pills |
| 18. | 100 I.U. | 15 mg. sodium chenodeoxycholate | aprotinin 3000 K.I.U. | enterocoated pills |
| 19. | 100 I.U. | 15 mg. sodium chenodeoxycholate | 5 mg. soybean trypsin inhibitor | enterocoated pills |

EXAMPLES 20 and 21

The following intercoated tablets were prepared in the following manner:

| Component | Example 20 | Example 21 |
|---|---|---|
| Insulin | 2 mg | 2 mg |
| Sod. Cholate | 15 mg | 15 mg |
| Trasilol | — | 1000 U |
| Lactose Hydrous USP | 144 mg | 150 mg |
| Starch NF | 36 mg | 30 mg |
| Magnesium Stearate NF | 3 mg | 3 mg |
| Eudragit L-100 (Polymer of Acrylic and Methacrylic Acid Esters) | 4 mg | 4 mg |
| Talc NF | 4 mg | 4 mg |
| Polyethylene Glycol 6000 NF | 0.4 mg | 0.4 mg |
| Total | 208.4 mg | 208.4 mg |

Method of Preparation:

(a) In order to homogeneously disperse the active components triturations with lactose for each component were individually prepared. Gradual dry mixing of all the components was then performed. The components are then mechanically pressed to form tablets of 9 mm diameter;

(b) A solution of the enterocoating polymer is then prepared by solving the polymer in a methylene chloride + isopropyl alcohol mixture. The tablets are coated by spraying the solution within a mildly warmed jar while the tablets roll. The solvent vapors are continuously aspirated.

Testing the Tablets

The dissolution of the tablets was then tested according to USP XX. The tablets were found to be stable for two hours in gastric juices. When they are then transferred to intestinal juices, they dissolve there in less than ½ an hour.

It will be evident to those skilled in the art that the invention is not limited to the details of the foregoing illustrative embodiments and examples and that the present invention may be embodied in other specific forms without departing from the essential attributes thereof, and it is, therefore, desired that the present embodiments and examples be considered in all respects as illustrative and not restrictive, reference being made to the appended claims, rather than to the foregoing description, and all changes which come with the meaning and range of equivalency of the claims are, therefore, intended to be embraced therein.

What is claimed is:

1. A pharmaceutical composition for the oral administration of insulin comprising insulin, a bile acid or alkali metal salt thereof which does not cause the damage to the cells of the intestinal wall caused by deoxycholic acid, said bile acid being selected fom the group consisting of sodium cholate cholic acid, chenodeoxycholic acid, taurocholic acid, taurochenodeoxycholic acid, glycocholic acid, glycochenocholic acid, $3\beta$-monohydroxychloric acid, lithocholic acid, $3\alpha$-hydroxy-12-ketocholic acid, $3\beta$-hydroxy-12-ketocholic acid, $12\alpha$-$3\beta$-dihydrocholic acid, and ursodesqxycholic acid, and a carefully screened and tested dosage amount of protease inhibitor, said composition being provided with an enterocoating to assure passage through the stomach and release of insulin in the intestine.

2. A pharmaceutial composition for the oral administration of insulin according to claim 1 wherein said protease inhibitor is selected from the group consisting of sodium cholate aprotinin, $A_2$-macroglobulin, antithrombin III and trypsin inhibitor from soy bean or chicken egg white.

3. A pharmaceutical composition for the oral administration of insulin according to claim 1 comprising sodium cholate as both the bile acid and the protease inhibitor.

4. A pharmaceutical composition for the oral administration of insulin according to claim 1 wherein the components of said composition are microencapsulated and enterocoated to provide for timed release of ingredients in the intestine.

* * * * *